United States Patent [19]

Lonardo

[11] Patent Number: 5,052,128
[45] Date of Patent: Oct. 1, 1991

[54] PADDED BOOT MEANS FOR INVALID PATIENTS

[75] Inventor: Robert Lonardo, 7360 137th St., N., Seminole, Fla. 34642

[73] Assignee: Robert Lonardo, Seminole, Fla. ; Trustee of the Robert Lonardo Living Trust Agreement

[21] Appl. No.: 383,454

[22] Filed: Jul. 24, 1989

[51] Int. Cl.$^5$ ............................ A43B 3/12; A61F 5/00
[52] U.S. Cl. ........................................ 36/11.5; 36/110; 128/83.5
[58] Field of Search ................ 36/110, 11.5, 9 R, 131, 36/132, 136, 91, 71, 114; 128/83.5

[56] References Cited

U.S. PATENT DOCUMENTS

| 1,637,565 | 8/1927 | Gordon | 36/132 |
| 1,667,629 | 4/1928 | Friedman | 36/9 R |
| 2,031,796 | 2/1936 | Stephens | 36/9 R |
| 2,205,091 | 6/1940 | Geffner | 36/11.5 |
| 2,742,717 | 4/1956 | Murray | 36/11.5 |
| 4,314,412 | 2/1982 | Anderson et al. | 36/11.5 |
| 4,361,972 | 12/1982 | Miller | 36/131 |
| 4,773,170 | 9/1988 | Moore et al. | 36/110 |

FOREIGN PATENT DOCUMENTS 3526298 1/1987 Fed. Rep. of Germany ........ 36/114

Primary Examiner—Steven N. Meyers
Attorney, Agent, or Firm—Zarley, McKee, Thomte, Voorhees, & Sease

[57] ABSTRACT

The padded boot means of this invention includes a padded boot having a first base portion, and having rearward and forward ends, and upper and lower surfaces. A secondary base portion is secured to the lower surface of the first base portion and is secured to the forward and rearward ends thereof to create a pocket there between. A supporting element such as the foot rest of a wheel chair, or a pad element, is adapted to be inserted into the pocket to support the patient's foot. The boot has lateral side portions which overlap on the upper portion of the patient's foot. Attachment means are provided for securing the side portions together. Similarly, the boot has a pair of heel flaps which extend from the rearward end of the boot, with the heel flaps being adapted to extend around a patient's heel. Attachment means serve to secure the heel flaps together. The boot has an outer surface comprised of a canvas-like material, and an inner surface comprised of a fleece-like material.

17 Claims, 2 Drawing Sheets

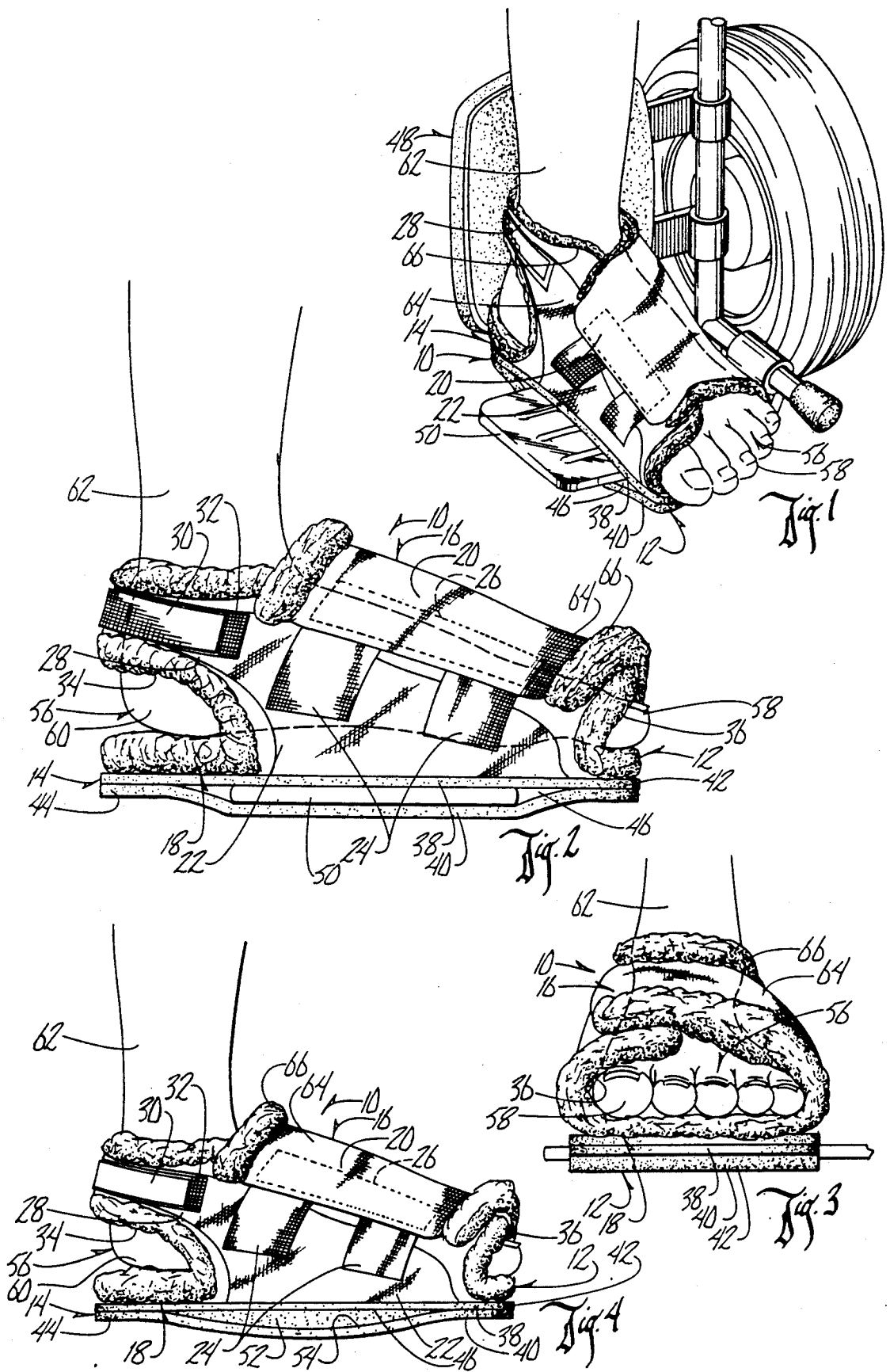

PADDED BOOT MEANS FOR INVALID PATIENTS

BACKGROUND OF THE INVENTION

Boots for invalid patients are common. They are normally equipped with a soft interior material for the comfort of the patient, and have securing straps or the like to facilitate attachment and detachment. Some such boots have suitable openings to receive splints or the like, as shown in U.S. Pat. No. 3,976,059.

However, existing boots are not versatile enough to secure a patient's foot to the foot rest portion of a wheel chair, and to also allow the sole of the boot to be supported for walking where a plurality of ambulatory problems exist. Further, many such boots will not receive both a normal sized foot, as well as a badly swollen foot.

Therefore, a principal object of this invention is to provide a boot means for invalid patients or the like which has a laterally open pocket means in the sole thereof to receive a supporting means whether it be the foot rest of a wheel chair or a pad means.

A further object of the invention is to provide a boot means for invalid patients or the like which is economical of manufacture, durable in use, and refined in appearance.

These and other objects will be apparent to those skilled in the art.

SUMMARY OF THE INVENTION

The padded boot means of this invention includes a padded boot having a first base portion, and having rearward and forward ends, and upper and lower surfaces. A secondary base portion is secured to the lower surface of the first base portion and is secured to the forward and rearward ends thereof to create a pocket there between. A supporting element such as the foot rest of a wheel chair, or a pad element, is adapted to be inserted into the pocket to support the patient's foot.

The boot has lateral side portions which overlap on the upper portion of the patient's foot. Attachment means are provided for securing the side portions together. Similarly, the boot has a pair of heel flaps which extend from the rearward end of the boot, with the heel flaps being adapted to extend around a patient's heel. Attachment means serve to secure the heel flaps together.

The boot has an outer surface comprised of a canvas-like material, and an inner surface comprised of a fleece-like material.

BRIEF DESCRIPTION OF THE DRAWINGS

FIG. 1 is a partial perspective view of the device of this invention mounted on a patient's foot and wherein the boot means is supported on the foot rest of a conventional wheel chair;

FIG. 2 is an enlarged scale side elevational view of the device of FIG. 1 as viewed from the left hand side of FIG. 1;

FIG. 3 is a front elevational view of the device of FIG. 2;

FIG. 4 is a side elevational view at a smaller scale similar to that of FIG. 2 but wherein the pocket means of the boot is filled with a suitable pad;

DESCRIPTION OF THE PREFERRED EMBODIMENT

Figure 5:
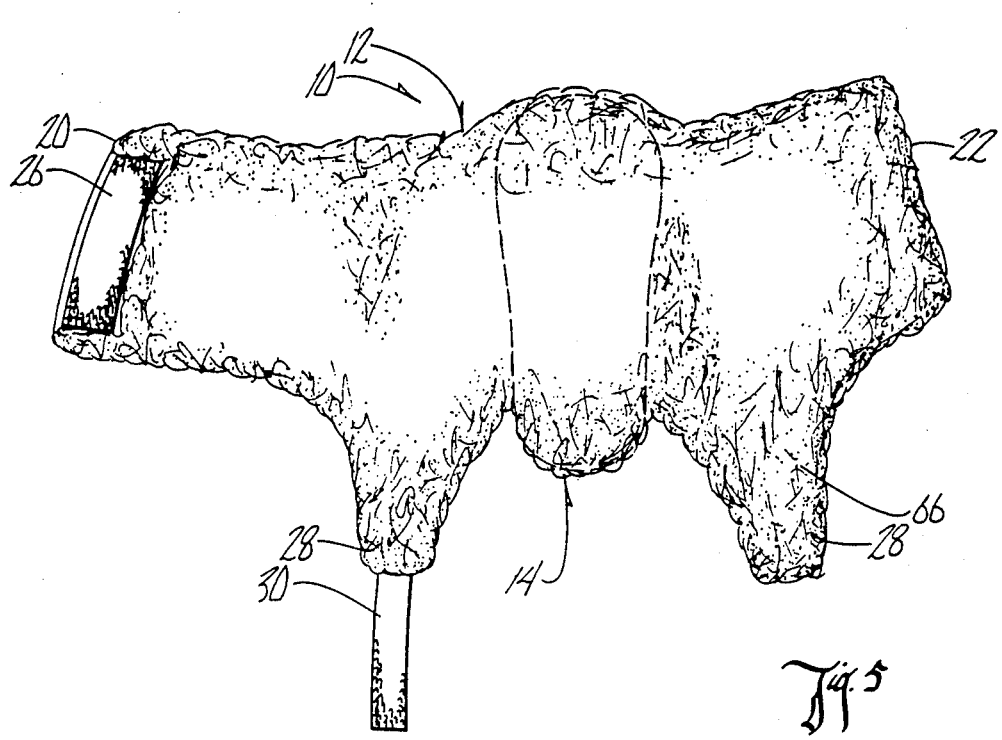
FIG. 5 is a plan view of the interior structure of the boot.
Figure 6:
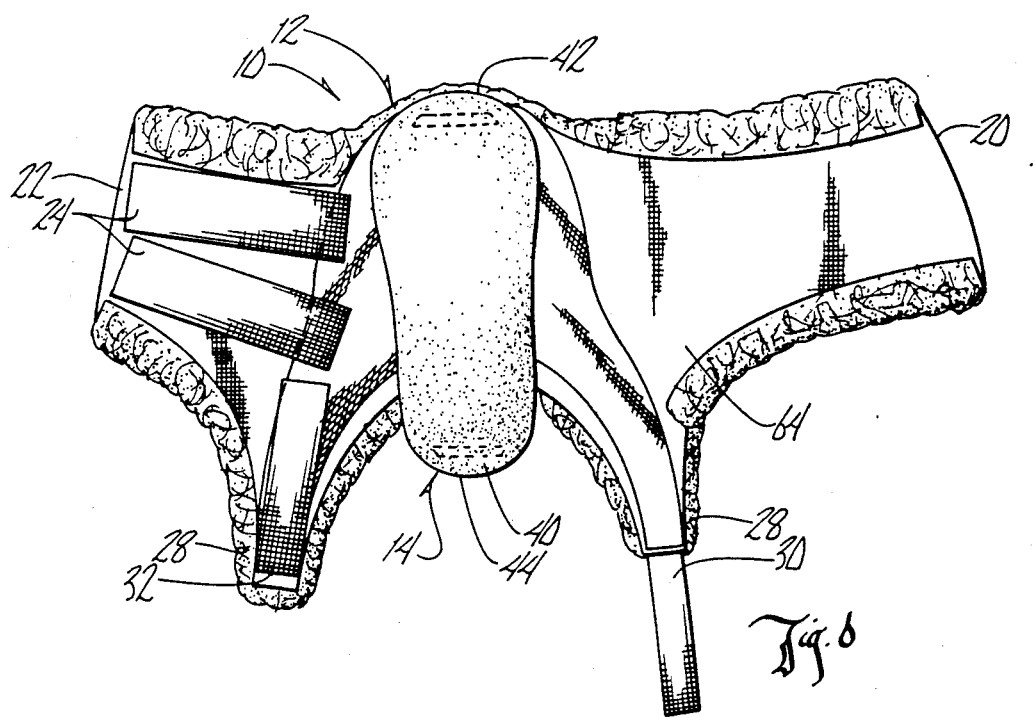
FIG. 6 is a plan view of the exterior surface of the boot.

Numeral 10 designates the boot of this invention which has a forward end 12, a rearward end 14, and upper surface 16, and a lower surface 18. Boot 10 includes side flaps 20 and 22 which are cooperatively detachably connected by detachable pressure (Velcro ®) fasteners 24 (FIG. 2) and 26 (FIG. 5). Heel flaps 28 extend rearwardly from the boot 10 and are adapted to be wrapped around a patient's heel and thereupon detachably secured together by conventional pressure (Velcro ®) fasteners 30 and 32.

The boot is provided with an open heel portion 34 and an open toe portion 36. These openings are provided by the heel flaps 28, and the side flaps 20 and 22, respectively.

A first base support 38 is secured to the outside lower surface 18 of boot 10 by adhesive or the like. A second base support 40 is secured to the lower portion of base support 38 by adhesive, stitching or the like at the forward and rearward ends 42 and 44 thereof. The first base support and the second base support are comprised of a flexible rubber material or the like. By being secured together only at the forward and rearward ends, a laterally open pocket 46 is created there between.

A conventional wheel chair 48 has a conventional laterally extending horizontal foot rest 50. The numeral 52 designates a pad with an arcuate lower surface 54. Alternatively, as will be described in more detail hereafter, the foot rest 50 can be moved laterally into pocket 46 to provide support for a patient sitting in the wheel chair. This arrangement also prevents the foot from becoming disengaged from the foot rest. Similarly, a pad of suitable configuration, such as pad 52, can be inserted into the pocket 46 (FIG. 4) to assist the walking activity of certain patients.

The numeral 56 designates a patient's foot having toes 58 heel 60 and lower leg 62.

The boot 10 is comprised of a canvas like material 64 as an exterior surface, with a fleece-like material 66 being present on the interior surface to provide comfortable padding for the patient's foot.

The boot 10 can be mounted on the patient's foot by affixing the side flaps and the heel flaps as described heretofore. If the patient is sitting in a conventional wheel chair, the foot rest 50 can be inserted in the pocket 48 as described previously to stabilize the patient's foot with respect to the foot rest.

Certain patients with various foot deformities may require assistance in the walking activity. Various pads having various thicknesses and configurations, such as pad 52, can be laterally inserted in pocket 46, to accommodate the particular problem or difficulty of the patient. Since the pocket 46 has lateral side openings, the insertion and removal of various pads from the pocket is facilitated.

If the patient's foot is swollen, the pressure fasteners attached to the side flaps of the boot and the heel portion of the boot can accommodate such a condition.

From the foregoing, it is seen that the device of this invention will achieve at least it's stated objectives.

I claim:

1. A padded boot for receiving an invalid patient's foot, the boot being worn for walking or for riding in a wheelchair, comprising:

a boot means for receiving a patient's foot, said boot means including a first base portion adapted to support the sole of the patient's foot and having rearward and forward ends and upper and lower surfaces, and a secondary base portion secured to the lower surface of said first base portion and secured to the forward and rearward ends thereof to create a pocket therebetween with open opposite sides extending substantially from the ball of the boot to the heel, whereupon a support means can be laterally inserted into and through said pocket to provide support for the patient's foot.

2. The boot of claim 1 wherein said secondary base portion is substantially the same size as said first base portion.

3. The boot of claim 1 wherein said pocket has closed forward and rearward ends.

4. The boot of claim 1 wherein a support means is inserted into said pocket, said support means being the foot support element of a wheelchair.

5. The boot of claim 1 wherein a support means is inserted into said pocket, said support means being a pad element.

6. The boot of claim 1 wherein said boot means has lateral side portions which comprise said upper surface which overlap on the upper portion of the patient's foot, and detachable means for securing said side portions together 7. The boot of claim 6 wherein a pair of heel flaps extend from the rearward end of said boot means, with said heel flaps being adapted to extend around a patient's heel, and means to detachably secure said heel flaps together.

8. The boot of claim 7 wherein the heel flaps are spaced from the first base portion so as to provide an open area adjacent the patient's heel.

9. The boot of claim 6 wherein said boot means has an outer surface comprised of a canvas-like material, and an inner surface comprised of a fleece-like material.

10. The boot of claim 7 wherein said boot means has an outer surface comprised of a canvas-like material, and an inner surface comprised of a fleece-like material.

11. The boot of claim 1 wherein said boot means has an outer surface comprised of a canvas-like material, and an inner surface comprised of a fleece-like material.

12. A padded boot for receiving an invalid patient's foot, the boot being worn for walking or for riding in a wheelchair, comprising:

a boot means for receiving a patient's foot, said boot means including a first base portion adapted to support the sole of the patient's foot and having rearward and forward ends and top and bottom surfaces, and including an upper boot portion extending across and being secured to the upper surface of the first base portion, the upper boot portion having a canvas-like outer surface, a fleece-like inner surface, opposite side portions for wrapping over the patient's foot, and means for securing the side portions together, such that the inner surface encircles the foot; and a secondary base portion secured to the bottom surface of said first base portion and secured to the forward and rearward ends thereof to create a pocket therebetween with open opposite sides extending substantially from the ball of the foot to the heel, whereupon a support means can be laterally inserted into and through said pocket to provide support for the patient's foot.

13. The boot of claim 12 wherein the upper boot portion further includes a pair of opposite heel flaps extending from the side portions and being adapted to extend around a patient's heel, and means to detachably secure said heel flaps together.

14. The boot of claim 13 wherein each heel flap includes a cut-out portion adjacent the first base portion to define an opening adjacent the patient's heel.

15. The device of claim 12 wherein said secondary base portion is substantially the same size as said first base portion.

16. The device of claim 12 wherein a support means is inserted into said pocket, said support means being the foot support element of a wheelchair.

17. The device of claim 12 wherein a support means is inserted into said pocket, said support means being a pad element.

* * * * *